US005946084A

United States Patent [19]

Kubulins

[11] Patent Number: 5,946,084

[45] Date of Patent: Aug. 31, 1999

[54] HEMISPHERICAL DOUBLE REFLECTION OPTICAL SENSOR

[75] Inventor: Vilnis E. Kubulins, Walton Hills, Ohio

[73] Assignee: Innovative Sensor Solutions, Ltd., Houston, Tex.

[21] Appl. No.: 09/013,451

[22] Filed: Jan. 26, 1998

[51] Int. Cl.[6] .......... G01N 21/41

[52] U.S. Cl. .......... 356/128; 356/136

[58] Field of Search .......... 356/128, 135, 356/136, 137

[56] References Cited

U.S. PATENT DOCUMENTS

| | | | |
|---|---|---|---|
| 4,274,705 | 6/1981 | Miller . | |
| 4,422,714 | 12/1983 | Benoit et al. . | |
| 4,427,293 | 1/1984 | Harmer | 356/136 |
| 4,440,022 | 4/1984 | Masom . | |
| 4,699,511 | 10/1987 | Seaver . | |
| 4,749,274 | 6/1988 | Aoki et al. . | |
| 4,803,470 | 2/1989 | Fineman . | |
| 4,895,444 | 1/1990 | Miyata et al. . | |
| 4,974,552 | 12/1990 | Sickafus . | |
| 4,998,022 | 3/1991 | Tregay . | |
| 5,026,139 | 6/1991 | Klainer et al. . | |
| 5,381,022 | 1/1995 | Nemeth et al. . | |
| 5,396,325 | 3/1995 | Carome et al. . | |
| 5,399,876 | 3/1995 | LaClair . | |

FOREIGN PATENT DOCUMENTS

| | | | |
|---|---|---|---|
| 2594-951-A | 8/1987 | France . | |
| 2694629 | 2/1994 | France | 356/136 |
| 64-38634 | 2/1989 | Japan | 356/136 |
| 1-170838 | 7/1989 | Japan | 356/136 |

OTHER PUBLICATIONS

Thin–Film Technologies Spur Revolution in Sensing, R & D Magazine, Jun. 1995.

'Micromirror' Optical Fiber Chemical Sensors, M.A. Butler, A. Ricco and K. B. Pfeifer. Government Inventions for Licensing, Reflectance–based optical fiber chemical sensor.

*Primary Examiner*—F. L. Evans
*Attorney, Agent, or Firm*—Fay, Sharpe, Beall, Fagan, Minnich & McKee, LLP

[57] ABSTRACT

An optical sensor for determining an index of refraction of a substance being monitored includes a light source (20). An optical element (24) having a coupling surface (30) and a measuring surface (26) is arranged such that light directed into the optical element (24) through the coupling surface (30) is partially reflected twice from the measuring surface such that it is directed to and exits through the coupling surface (30). The measuring surface (26) is preferably spherical. An input optical fiber (22) having first and second ends directs light emitted from the light source to the coupling surface of the optical element. The first and second ends of the input optical fiber (22) are optically coupled to the coupling surface (30) of the optical element (24) and the light source, respectively. An output optical fiber (28) has first and second ends and directs light expelled from the coupling surface (30) of the optical element (24) to a photodetector (50). The first and second ends of the output optical fiber (28) are optically coupled to the coupling surface (30) of the optical element (24) and the photodetector, respectively. The amount of light that is partially reflected at each reflection from the measuring surface (26) is dependent upon the difference between the index of refraction of the optical element (24) and the index of refraction of the substance being monitored (12) which is adjacent the measuring surface (26) of the optical element.

19 Claims, 10 Drawing Sheets

HEMISPHERICAL DOUBLE REFLECTION OPTICAL SENSOR

BACKGROUND OF THE INVENTION

The present invention relates generally to the art of optical sensors. It finds specific application in conjunction with optical sensors for determining the presence and/or index of refraction of a medium in which the optical sensor may be immersed or placed in contact, and will be described with particular reference thereto. However, it is to be appreciated that the invention will also find further application in other optical devices.

Heretofore, numerous types of optical sensors responsive to the index of refraction have been developed. In such prior sensors, light from a reference light source entered an optical element and was either transmitted into a surrounding medium or internally reflected within the optical element and channeled to a readout apparatus. Frequently, optical fibers provided the channels to direct light from a light source into the optical element and return internally reflected light to the photodetector or other readout device. Although a wide variety of sensors based on this approach have been developed, they have significant disadvantages.

In one prior optical sensor illustrated in U.S. Pat. No. 5,396,325 of Carome and Rainer, the optical element included a flat sapphire plate to which a pair of optical fibers were coupled. The optical fibers were connected to the flat plate at carefully prescribed locations and angles such that light emitted from the first strikes a common central plane and is received at the other, all with prescribed angles of incidence and reflection. One of the disadvantages of this sensor resides in the complexity of manufacture. The attaching of optical fibers at prescribed oblique angles in a spaced relationship to a flat plate is laborious and difficult to mechanize. Moreover, the resultant sensors tended to be relatively delicate. Another disadvantage of this sensor is that increasing the index of refraction of the flat plate does not increase the range of indices that can be sensed.

In another prior art device illustrated in U.S. Pat. No. 4,274,705 of Miller, the optical sensor is a hemi-ellipsoid. The optical fibers are positioned precisely at the two foci of the ellipse. One advantage of the hemi-ellipsoidal construction is that the monitored index is a function of the index of refraction of the optical sensor material. This permits the monitoring of materials with indices of refraction well above the index of refraction of the fiber core. However, the precise placement of the optical fibers at oblique angles against a flat surface is difficult and laborious. Again, the resultant detector tends to be relatively delicate.

In another prior art device described in French Patent No. 2 594 951 to Remouit, the optical sensor is characterized by a single reflection from the measuring surface. An inherent disadvantage of the optical sensor described in the French Patent to Remouit is its lack of sufficient sensitivity to changes in the index of refraction of the substances being monitored.

Another difficulty with many of the prior art optical sensors is that their outputs are not reliable and are difficult to interpret.

The present invention provides a new and improved optical sensor and refractometer arrangement which overcomes the above-referenced problems and others.

SUMMARY OF THE INVENTION

In accordance with one aspect of the present invention, an optical sensor for determining an index of refraction of a substance being monitored is provided. The optical sensor includes a light source and an optical element having a coupling surface and a measuring surface. Light directed into the optical element through the coupling surface is partially reflected twice from the measuring surface such that it is directed to and exits through the coupling surface. An input optical fiber is optically coupled at a first end to the coupling surface of the optical element and at a second end to the light source. The input optical fiber directs light emitted from the light source into the optical element through the coupling surface thereof. An output optical fiber is optically coupled at a first end to the coupling surface of the optical element and at a second end to a photodetector. The output optical fiber directs light exiting the coupling surface of the optical element to the photodetector.

In accordance with a more limited aspect of the present invention, the amount of light that is partially reflected at each reflection from the measuring surface is dependent on a difference between the index of refraction of the optical element and the index of refraction of the substance being monitored which is adjacent the measuring surface of the optical element.

In accordance with a more limited aspect of the present invention, the optical element is a plano-convex lens having a planar surface and convex surface such that the planar surface is the coupling surface and the convex surface is the measuring surface.

In accordance with a more limited aspect of the present invention, the convex measuring surface is a substantially spherical surface segment.

In accordance with a more limited aspect of the present invention, the optical element is made of sapphire.

In accordance with a more limited aspect of the present invention, the input and output optical fibers are arranged such that central axes of their first ends are parallel and lie in a plane that is orthogonal to a plane defined by the coupling surface of the optical element.

In accordance with a more limited aspect of the present invention, the first ends of the input and output optical fibers are positioned symmetrically on opposite sides of and equidistant from a center of the coupling surface.

In accordance with a more limited aspect of the resent invention, the first ends of the input and output optical fibers are arranged such that extensions of their central axis intersect the measuring surface at 45 degrees relative to a normal of the measuring surface at the intersection points.

In accordance with a more limited aspect of the present invention, the light source is a light emitting diode.

In accordance with a more limited aspect of the present invention, the measuring surface of the optical element is coated with a coating that interacts with a preselected target substance thereby changing its reflectivity.

In accordance with a more limited aspect of the present invention, circuitry is connected to the photodetector to receive a signal therefrom which corresponds to an amount of light received by the photodetector. The circuitry compares the signal received while the measuring surface is in contact with the substance being monitored to a known value which would be received were the measuring surface in contact with a calibration substance having a known index of refraction.

In accordance with a more limited aspect of the present invention, the circuitry addresses a corresponding index of refraction from a table which maps a ratio of the signal received to known values on a scale versus index of refraction.

In accordance with a another aspect of the present invention, a method of sensing the index of refraction of a monitored substance is provided. The method includes generating light and directing the light to a first surface of an optical element. The light is transmitted into the optical element through the first surface and directed to a second surface of the optical element which is in contact with the substance being monitored. A portion of the light is transmitted into the substance and the remaining portion of the light is reflected. The remaining portion of the light is then directed to another portion of the second surface of the optical element. Again, a portion of the light is transmitted into the substance and the remaining portion of the light is reflected. The remaining portion of the light is directed to the first surface of the optical element. The light is expelled from the optical element through the first surface and the amount of expelled light is measured.

In accordance with a more limited aspect of the present invention, the portion of the light transmitted into the substance is dependent upon a difference between indices of refraction of the optical element and the substance being monitored.

In accordance with a more limited aspect of the present invention, prior to performing the method on the monitored substance, the method is performed or a calibration substance having a known index of refraction. The measurement received thereby is stored in a memory. After performing the method on a monitored substance, the ratio of the measurement from the monitored substance to the stored measurement is computed. A corresponding index of refraction of the substance being monitored is retrieved from a table which maps the computed ratio on a scale versus index of refraction.

In accordance with a more limited aspect of the present invention, the light is directed to a first region which lies within one-half of the second surface of the optical element for the first transmitting and reflecting step and is directed to a second region which lies within an opposite half of the second surface of the optical element for the second transmitting and reflecting step.

In accordance with another aspect of the present invention, an optical sensor for determining an index of refraction of a substance being monitored is provided. The optical sensor includes a light source and an optical element having a planar coupling surface and a spherical measuring surface. Light directed into the optical element through the planar coupling surface is at least partially reflected once from a first region of the spherical measuring surface and at least partially reflected again from a second region of the spherical measuring surface such that it is directed to and exits through the planar coupling surface. An optical input device has a first end optically coupled to the planar coupling surface of the optical element and a second end optically coupled to the light source. The optical input device directs light emitted from the light source into the optical element through the planar coupling surface. An optical output device has a first end optically coupled to the planar coupling surface and a second end optically coupled to a photodetector. The optical output device directs light exiting the planar coupling surface of the optical element to the photodetector.

In accordance with a more limited aspect of the present invention, one of the first and second regions of the spherical measuring surface is mirrored and the light is fully reflected. The other of the first and second regions of the spherical measuring surface is not mirrored and the light is partially reflected.

In accordance with a more limited aspect of the present invention, the optical input device is a fiber optic bundle including a plurality of individual optical fibers arranged adjacent one another and the optical output device is a fiber optic bundle including a plurality of individual optical fibers arranged adjacent one another.

In accordance with a more limited aspect of the present invention, the optical input device includes a plurality of input optical fibers spaced apart from one another and the optical output device includes a plurality of output optical fibers spaced apart from one another. The input and output optical fibers have a one-to-one correspondence and are arranged symmetrically on opposite sides of a center of the planar coupling surface of the optical element such that light fed into the optical element from each input optical fiber is received by its corresponding output optical fiber opposite therefrom.

In accordance with another aspect of the present invention, an optical sensor for determining an index of refraction of a substance being monitored is provided which includes a light source. An optical element having first and second surfaces and an index of refraction is optically coupled with the light source such that the light from said light source enters the optical element through the first surface, it interfaces with the second surface which is in contact with the substance being monitored changing the amount of light remaining in the optical element, and thereafter the light remaining in the optical element exits the optical element through the first surface. A photodetector is optically coupled with the optical element such that it receives the light exiting the optical element through the first surface. When the substance being monitored has an index of refraction equal to the index of refraction of the optical element, the light interfacing with the second surface is transmitted through the second surface leaving substantially no remaining light in the optical element. When the substance being monitored has an index of refraction different from the index of refraction of the optical element, the light interfacing with the second surface is at least partially reflected twice from the second surface leaving at least some remaining light in the optical element to be measured.

In accordance with a more limited aspect of the present invention, at least one of the light source and the photodetector is mounted directly to the first surface of the optical element.

In accordance with a more limited aspect of the present invention, at least one of the light source and the photodetector is optically coupled to the optical element via at least one optical fiber.

In accordance with a more limited aspect of the present invention, an amount of light reflected at each partial reflection from the second surface is dependent upon a difference between the index of refraction of the optical element and the index of refraction of the substance being monitored.

In accordance with a more limited aspect of the present invention, the optical element is a plano-convex lens having a planar surface and a convex surfaced such that the planar surface is the first surface and the convex surface is the second surface.

One advantage of the present invention resides in its simplicity of construction.

Another advantage of the present invention is its well defined high sensitivity to changes in the index of refraction of a monitored sample.

Another advantage of the present invention resides in its size.

Another advantage of the present invention resides in its relatively rugged construction.

Yet another advantage of the present invention resides in its ability to measure indices of refraction above the index of refraction of the optical fiber cores.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
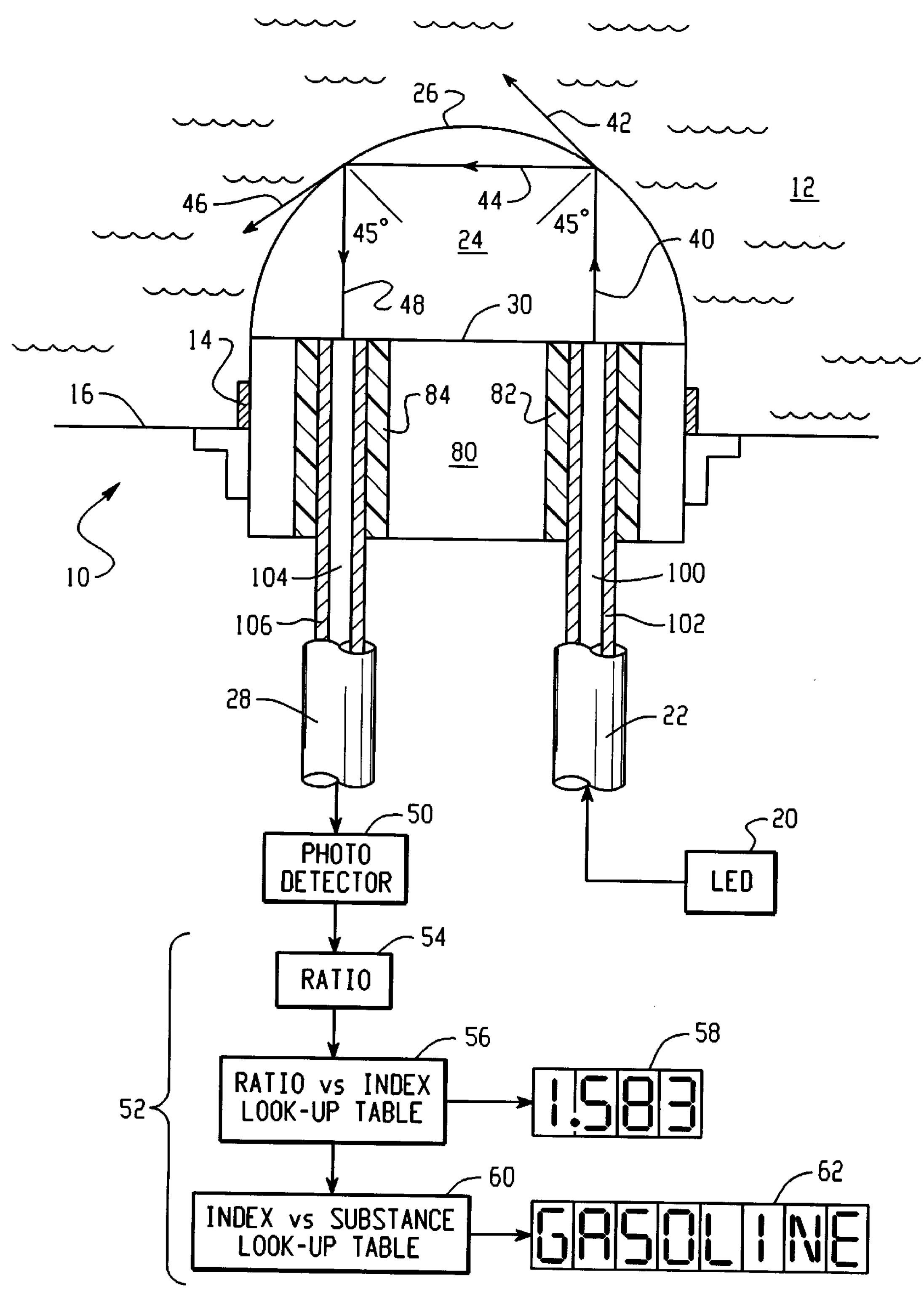
FIG. 1 is a diagrammatic illustration of an optical sensor system in accordance with the present invention.

With reference to FIG. 1, an optical sensor 10 is positioned to be immersed in a substance 12 to be monitored or measured, such as a liquid or gas. For example, the optical sensor 10 may be mounted, via threads 14, in the side wall 16 of a chemical, biomedical, food processing, or other fluid systems to monitor properties of fluids being processed or flowing through a pipeline. In one preferred embodiment, the optical sensor 10 is positioned in drainage channels around petroleum storage tanks to monitor for petroleum contamination in run-off water.

A light source such as an LED 20 transmits light along an input optical fiber 22. The input optical fiber 22 is optically coupled with a generally hemispherical optical element 24, for example a plano-convex lens, of the optical sensor 10. A spherical measuring surface 26 of the optical element is immersed in the substance 12 to be monitored. Based on the relative indices of refraction of the substance 12 and the optical element 24, different fractions of the light will either escape into the substance 12 or be reflected twice back into an output optical fiber 28 that is also coupled with the optical element 24.

More specifically, the LED 20 is optically coupled with one end of the input optical fiber 22. Light generated by the LED 20 is directed along the length of the input optical fiber 22 to the other end which is optically coupled with a coupling surface 30 of the optical element 24. The light 40 entering the optical element 24 through the coupling surface 30, represented by its central axial ray, proceeds to the measuring surface 26 where it is partially reflected. A portion of the light 42, represented by its central axial ray, is transmitted into the substance 12 being monitored which is adjacent the measuring surface 26. The remaining light 44, represented by its central axial ray, is reflected at the measuring surface 26 and remains within the optical element 24. The remaining portion of the light 44 again proceeds to the measuring surface 26. Again, the light is partially reflected at measuring surface 26. A portion of the light 46, represented by its central axial ray, is transmitted into the substance 12 and a remaining portion 48, represented by its central axial ray, is reflected. After the two partial reflections, the remaining light 48 proceeds to the coupling surface 30 of the optical element 24. One end of output optical fiber 28 which is optically coupled to the coupling surface 30 of the optical element 24 receives the remaining light 48 as it is expelled from the optical element 24 through the coupling surface 30. The output optical fiber 28 directs the light along its length to the other end which is optically coupled to a photodetector 50. The photodetector 50 generates an electrical signal which corresponds to the amount of light received from the output optical fiber 28. Circuitry 52 connected to the photodetector to receive the electrical signal therefrom compares the signal to a known value which would have been received were the measuring surface 26 in contact with a calibration substance having a known index of refraction.

More specifically, the circuitry 52 includes a ratio circuit 54 which determines a ratio of the received signal to the known value. The ratio is used to address a look-up table or other ratio to refractive index determining device 56. The index of refraction retrieved from the look-up table, in one embodiment, is displayed on a read out device 58. In an alternate embodiment, the read out index of refraction addresses a second look-up table 60 which relates the index of refraction to common substances. For example, common petroleum products such as gasoline, motor oil, kerosene, heating oil, and the like, each have a characteristic index of refraction. The look-up table 60 is preprogrammed with a range of indices of refraction corresponding to each of a plurality of substances for which the system is monitoring. Indices which do not correspond to any monitored substance may be designated as "other" or another term to connote that the monitored index does not correspond to any of the monitored substances. An alphanumeric display unit 62 converts the retrieved substance into an alpha or alphanumeric display indicative of the substance currently covering the measuring surface 26 of the optical element 24.

Figure 2:
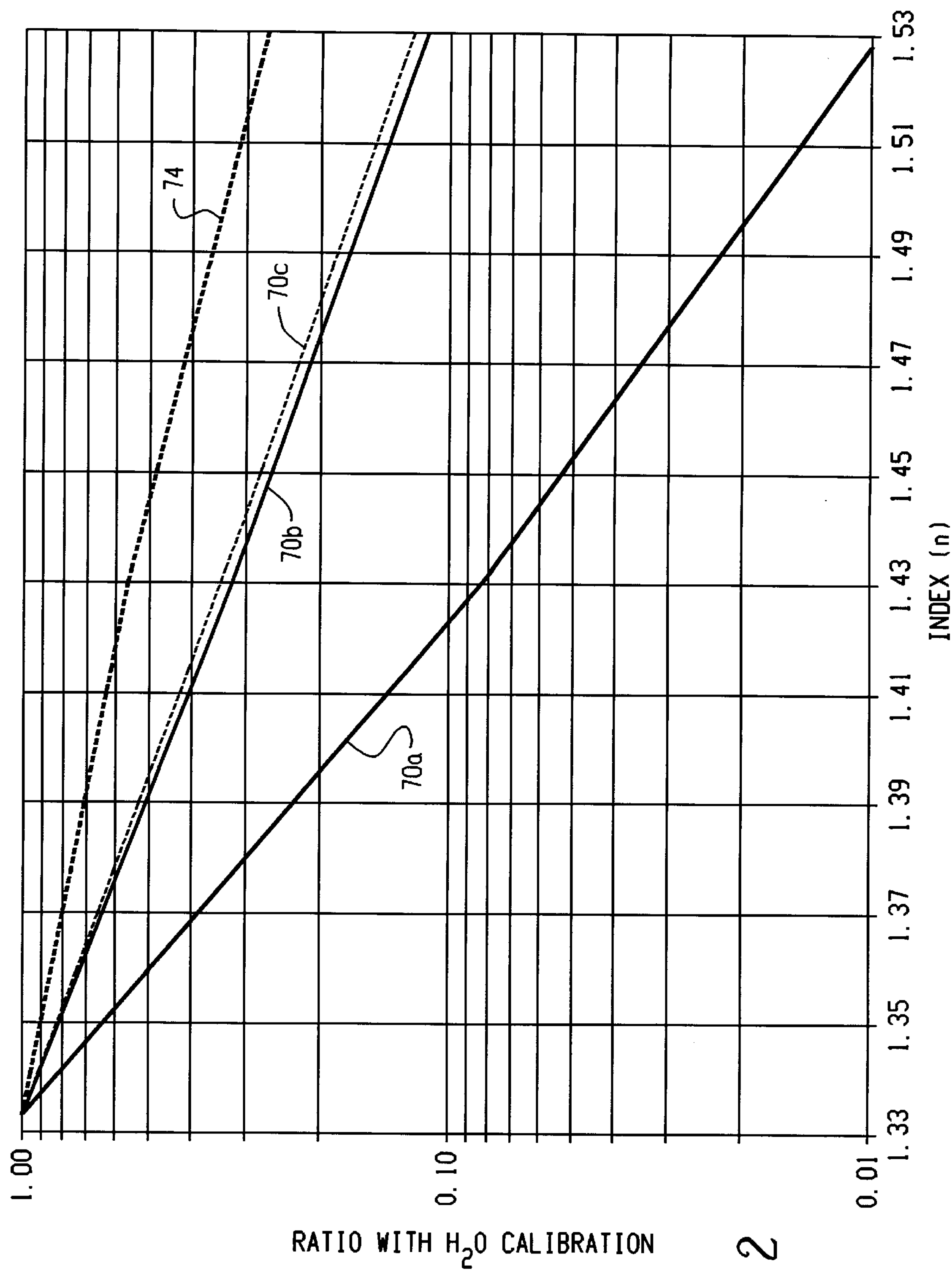
FIG. 2 illustrates the relationship between index of refraction and the ratio of a signal received when the optical sensor is in contact with a substance being monitored to a known value which would be received were the optical sensor in contact with a calibration substance having a known index of refraction.

With reference to FIG. 2 and continuing reference to FIG. 1, with the optical sensor 10 of the preferred embodiment over a wide range of variations of the index of refraction, the logarithm of the ratio of the light returned when the sensor is immersed in a substance 12 being measured or monitored, to the returned light when the sensor is immersed in a calibration substance, such as air or water, has a substantially linear relationship relative to the index of refraction of the substance 12 being monitored. In a preferred embodiment, the look-up table 56 is preprogrammed to be addressed with values along a ratio axis and read out the corresponding values of the index of refraction along a line or curve 70. It might be noted that with a flat optical element, such as the one illustrated in prior U.S. Pat. No. 5,396,325, the light returned to the photodetector 50 decays to zero at the point where the index of refraction of the monitored substance 12 equals that of the core material of the optical fibers 22, 28, e.g., for silicon glass cores around an index of refraction of 1.46. Note also, with reference to FIG. 2, that the slopes of curves 70*a–c* (corresponding to embodiments of applicant's present invention) are greater than the slope of the curve 74 corresponding to representative results achieved by sensors consistent with those described in the French Patent No. 2 594 951 to Remouit. In order to permit a legitimate comparison, curves 70*a–c* and 74 represent results achieved by the respective sensor when analogously configured. This illustrates the increased sensitivity to changes in the index of refraction of applicant's sensor as compared to that of the French Patent to Remouit. In particular, 70*a* corresponds to the embodiments described herein with two partial reflections at the measuring surface 26, and 70*b* and 70*c* correspond to embodiments described later herein with one partial reflection and one full reflection.

Figure 3:
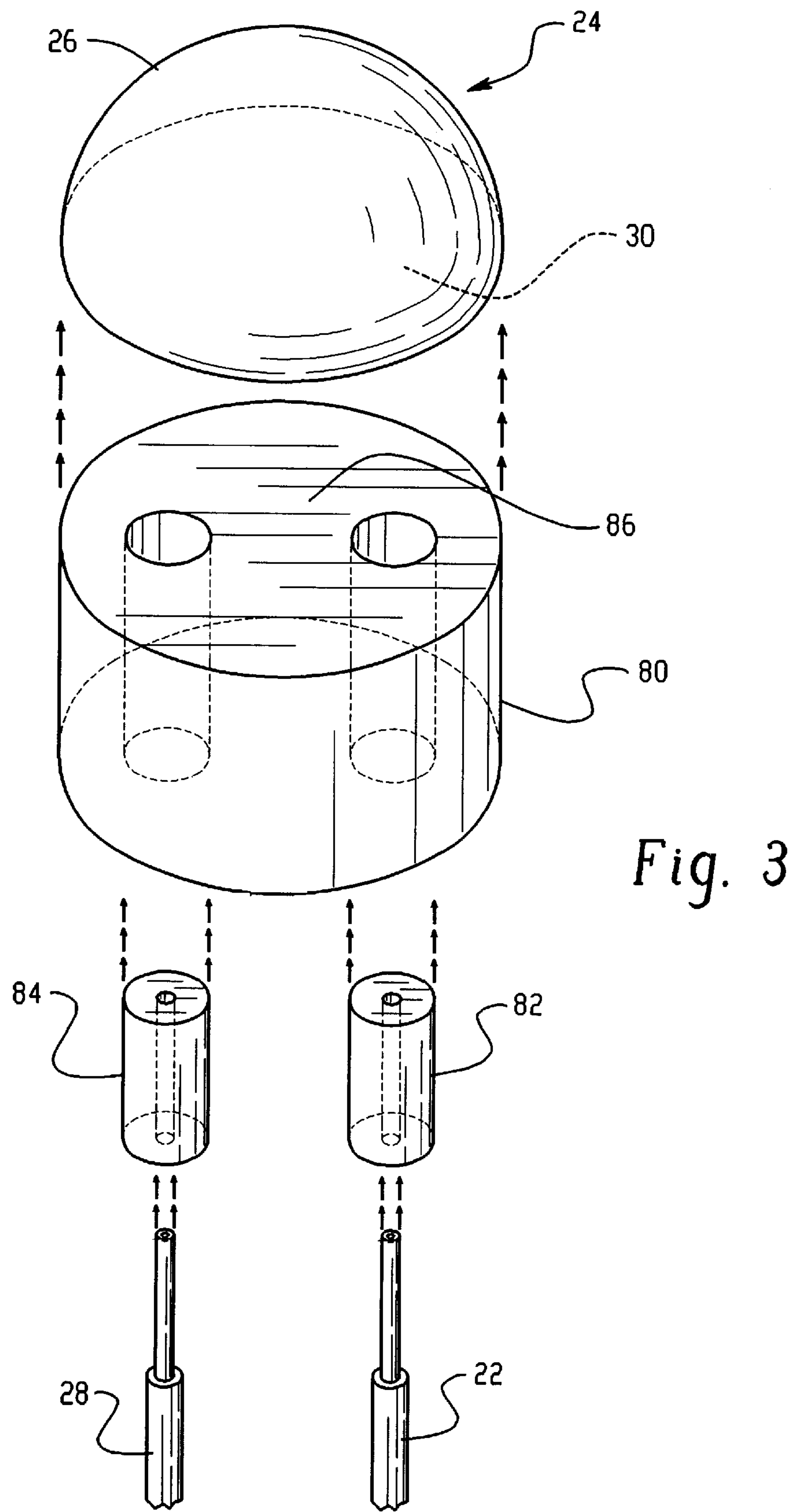
FIG. 3 is an exploded view of the optical sensor in accordance with aspects of the present invention which illustrates a preferred mode of construction.

With continuing reference to FIG. 1 and further reference to FIG. 3, in a preferred method of assembly, a cylindrical plug 80 (made of brass in an exemplary embodiment) has two parallel axial bores drilled therein which lie equidistant from the center axis of the plug. Capillary tubes 82 and 84 are secured within the axial bores of the plug 80. Ends of the input and output, optical fibers 22, 28 are stripped of their outer jackets and tightly secured within capillary tubes 82 and 84 respectively. The outer diameter of the capillary tubes 82, 84 match the inner diameter of the axial bores. The coupling end 86 of the assembly is then lapped and polished. The coupling surface 30 of the optical element 24 is joined to the coupling end 86 using an adhesive (heat curing epoxy in an exemplary embodiment). Prior to the setting of the adhesive, the optical element 24 is slid around over the coupling end 86 of the optical fiber and plug assembly with light propagating through the sensor 10. When the photodetector 50 receives a peak signal, the optical element 24 is accurately aligned and optically coupled with the ends of the input and output optical fibers 22, 28 such that the optical element directs the input light from the input optical fiber 22 to the end of the output optical fiber 28 after two partial reflections from the measuring surface 26. The adhesive is then cured fixing this alignment.

Figure 4:
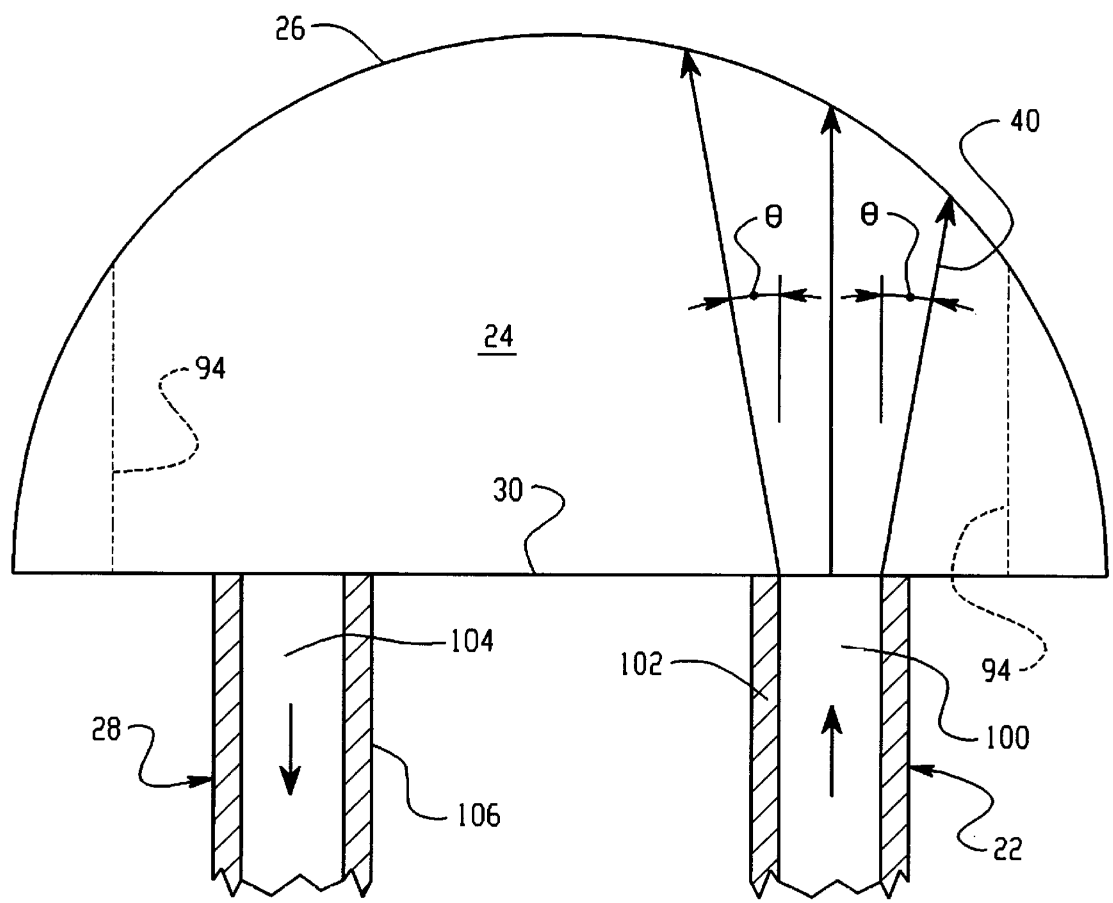
FIG. 4 is a diagrammatic illustration of the optical element in accordance with the present invention.

With continuing reference to FIGS. 1 and further reference to FIG. 4, the optical element 24 may be a cylindrical section 94 formed from a sphere. In an exemplary embodiment the sphere has a diameter of about 5 mm. The flat, lapped and polished coupling surface 30, may be defined at, above, or below a central diameter of the sphere. Of course, the optical element can be made such that the flat surface 30 and the cylindrical surface 94 are defined as the optical element 24 is originally manufactured. Alternately, the optical element 24 may be any plano-convex lens with or without the cylindrical surface 94.

The input optical fiber 22 has a central core 100, preferably of a silicon glass which ha., an index of refraction of about 1.46–1.48. The core is surrounded by lower index of refraction cladding 102. The optical element preferably is of a material with a higher index of refraction, such as sapphire, with an index of refraction of about 1.77. Because the core 100 and the flat coupling surface 30 of the optical element 24 are perpendicular and the surface 30 is nearly perpendicular to all incident radiation from the core 100, a substantial portion of the light enters the optical element 24. With a core 100 having an index of refraction of about 1.46 and an optical element 24 having an index of refraction of about 1.77, the light entering the optical element 24 spreads with a half-angle $\theta$ of about 12°. The output fiber 28 analogously has a light conductive core 104 surrounded by a lower index cladding 106. The optical fiber cores are about 200 microns in diameter for an exemplary embodiment. The optical cores are spaced symmetrically about the geometric center of the spherical optical element 24.

In a preferred embodiment, the input and output optical fibers 22, 28 are arranged such that the central axes of the ends coupled to the optical element 24 are parallel to one another, lie in a plane that is orthogonal to the plane defined by the coupling surface 30, and are normal to the plane defined by the coupling surface 30 of the optical element 24. The input and output optical fibers 22, 28 are positioned symmetrically on opposite sides of and equidistant from the center of the coupling surface 30. Extensions of the central axis intersect the measuring surface 26 at a 45° angle relative to the normal of the measuring surface 26 at the points of intersection.

Figure 5A:
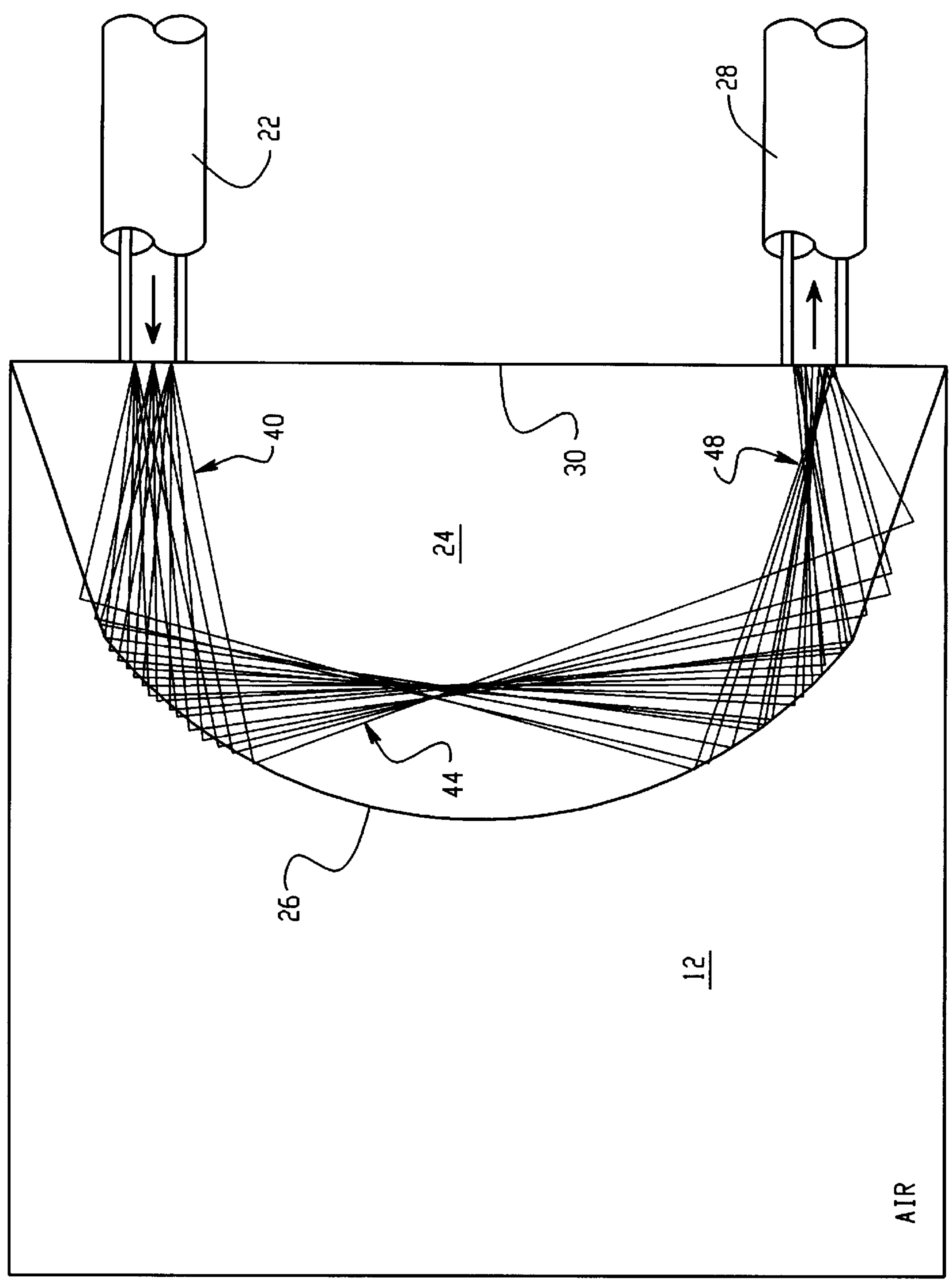
FIGS. 5A and 5B are ray diagrams illustrating the paths of the light rays when the measuring surface of the optical element in accordance with the present invention is in contact with air and water, respectively.
Figure 5B:
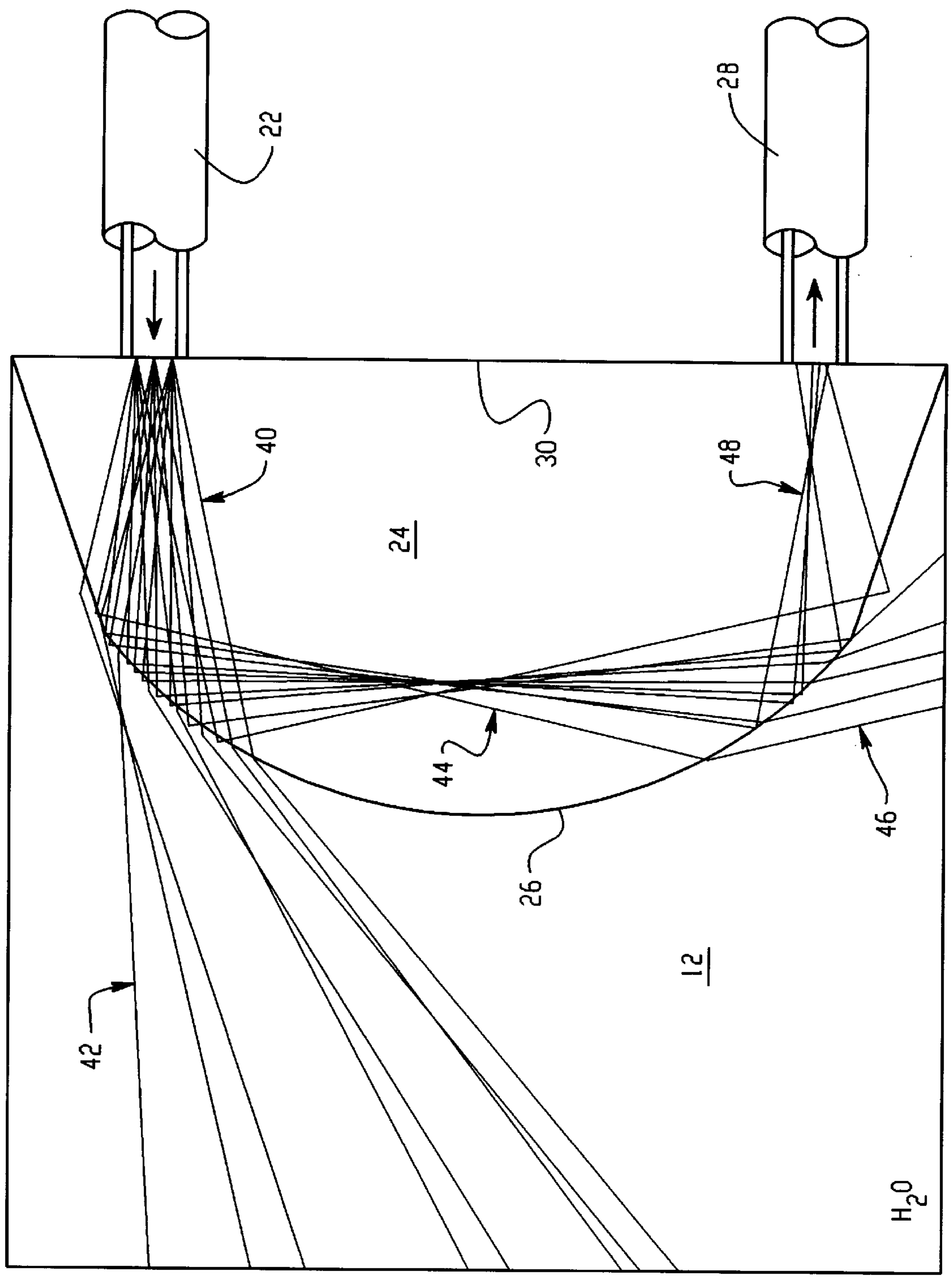

FIGS. 5A and 5B are ray diagrams detailing the paths of the light rays when the measuring surface 26 of the optical element 24 is in contact with air and water, respectively. When in contact with air, the light 40 from the input optical fiber 22 is totally internally reflected twice from the measuring surface 26 and directed into the output optical fiber 28. When the measuring surface 26 of the optical element 24 is in contact with a monitored substance 12, in this case water, the light 40 from the input optical fiber 22 is only partially reflected at the measuring surface 26. A portion of the light 42 is transmitted and a portion of the light 44 is reflected. The light 44 is then again partially reflected at the measuring surface 26. A portion of the light 46 is transmitted and a portion of the light 48 is reflected and directed into the output optical fiber 28. The multiple partial reflections contribute to the increased sensitivity of the optical sensor 10.

Figure 6A:
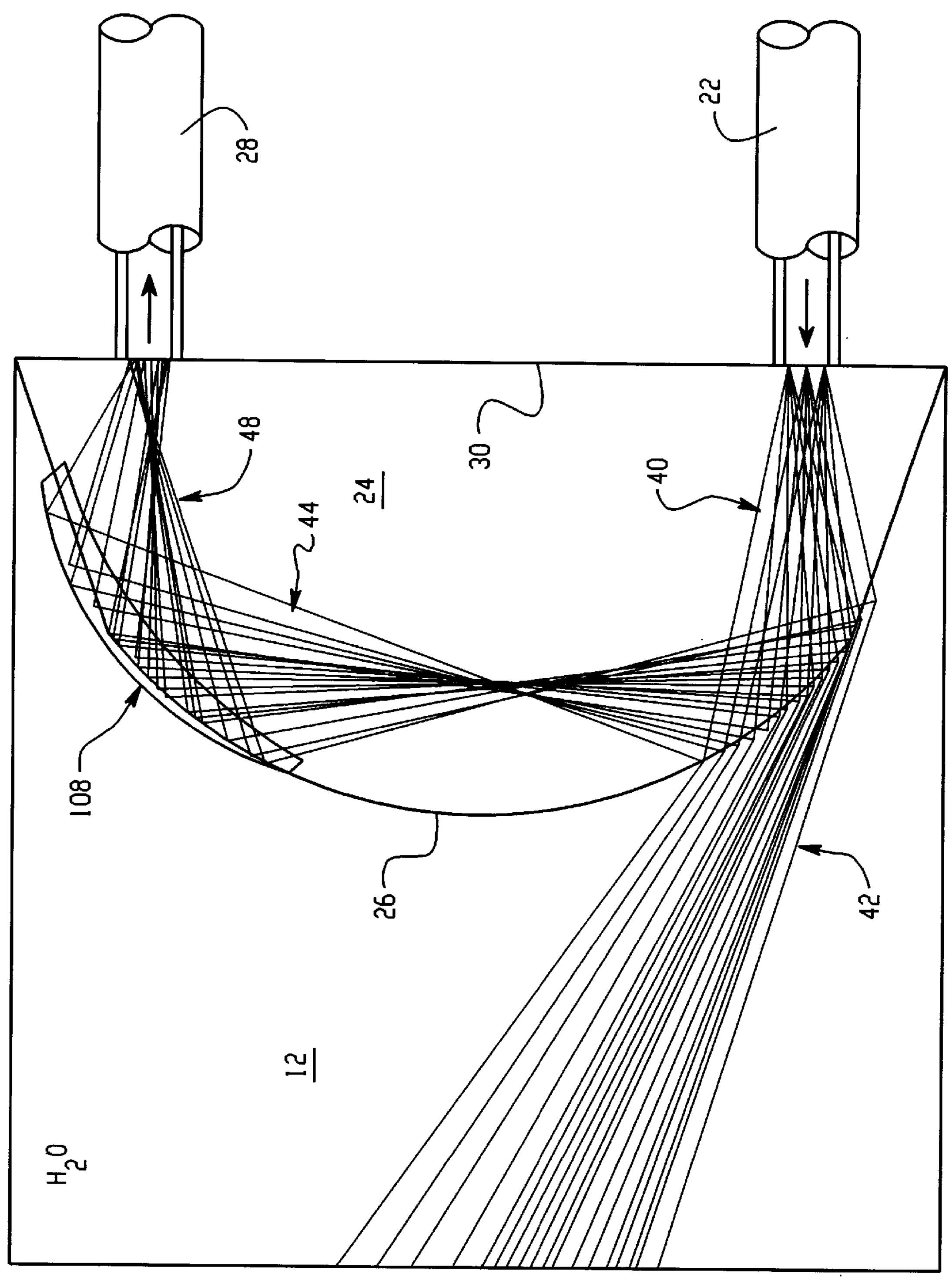
FIGS. 6A and 6B are ray diagrams illustrating the optical paths of light in accordance with another embodiment of the present invention.
Figure 6B:
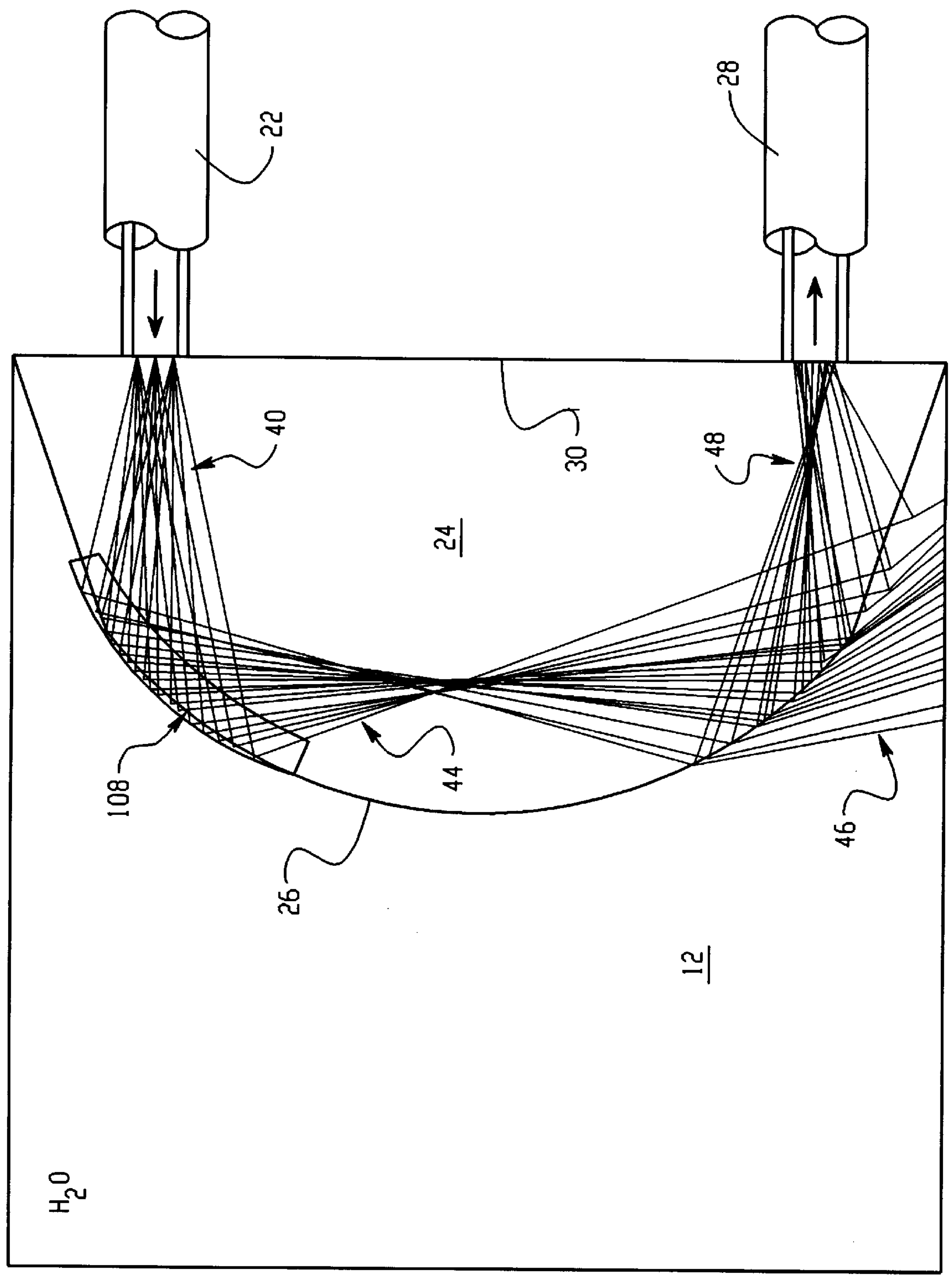

With reference to FIGS. 6A and 6B, ray diagrams detail the optical paths of another embodiment of the optical sensor 10. In this embodiment, a mirrored portion 108 of the measuring surface 26 of the optical element 24 converts one of the partial reflections into a total reflection. The mirrored portion 108 may be at the first reflection from the measuring surface 26 or the second reflection from the measuring surface 26. In this embodiment, the sensitivity of the optical sensor 10 is traded for an increase in the overall light returned to the output optical fiber 28. In any case, the sensitivity is still greater than that of an analogously configured sensor of the type discussed in the French Patent to Remouit, as seen in FIG. 2. Plot 70*b* corresponds to the embodiment of the present invention where the mirror is on the input side (FIG. 6B) and plot 70*c* corresponds to the embodiment of the present invention where the mirror is on the output side (FIG. 6A). Both plots 70*b* and 70*c* have greater slopes than plot 74 (corresponding to the Remouit Patent) illustrating that for the same change in index of refraction there is a corresponding greater change in the logarithm of the ratio of the signal received to the known value which would be received were the sensor immersed in a calibration substance.

Figure 7:
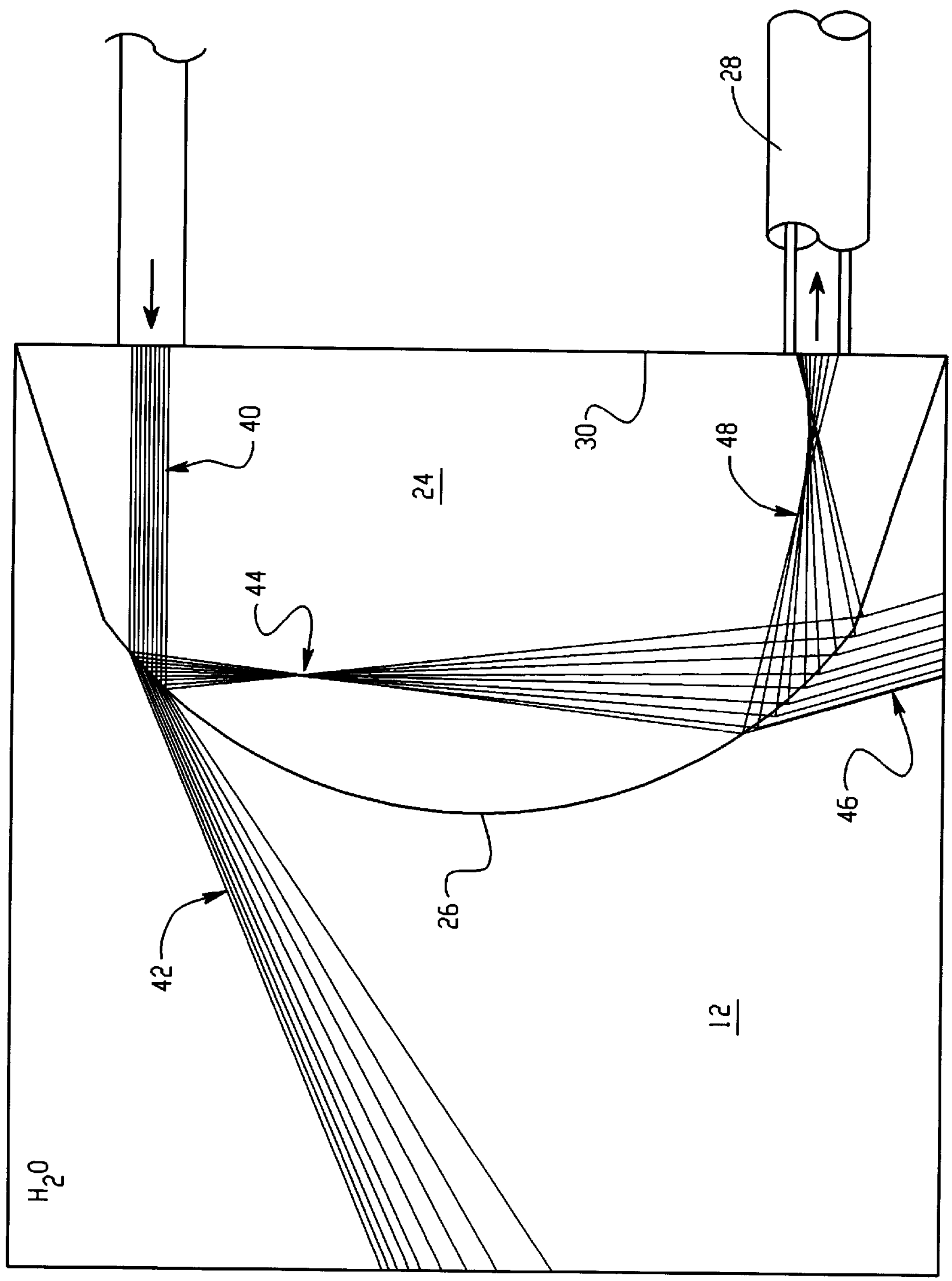
FIG. 7 is a ray diagram illustrating the optical paths of the light in accordance with another embodiment of the present invention.

With reference to FIG. 7, a ray diagram details the optical paths of another embodiment of optical sensor 10. In this embodiment, the input optical fiber 22 is not employed. Rather, a collimated beam of light is input into the optical element 24 through the coupling surface 30. By employing the collimated beam with minimal-to-no spread angle, the function of directing the light from the light source 20 and coupling it into the optical element 24 through the coupling surface 30 is achieved without the use of an input optical fiber 22.

Figure 8:
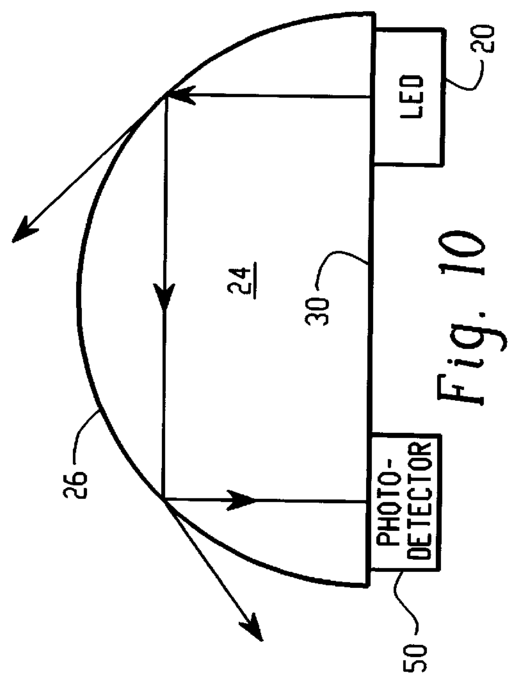
FIG. 8 is a diagrammatic illustration of the optical sensor in accordance with the present invention wherein the measuring surface of the optical element is coated with a material that changes its reflectivity when it interacts with a preselected substance.

With reference to FIG. 8, the optical element 24 is coated with a material 110 which changes its reflectivity when it interacts with a preselected fluid. For example, the coating material 110 may be a thin gold film which reflects light within the optical element 24. When mercury in the sensed fluid comes in contact with the gold film, the mercury wets the gold film and dissolves it, changing its light reflective characteristics. In this manner, a change in the sensed reflectivity is indicative of the presence of mercury. As another example, the film 110 may be a thin silver film. Silver reacts readily with hydrogen sulfide, changing its reflective properties. Analogously, a palladium coating can be used to detect hydrogen gas. Other coatings which react with or are selectively dissolvable by a preselected potential component within the monitored substance 12 can also be utilized.

Figure 9A:
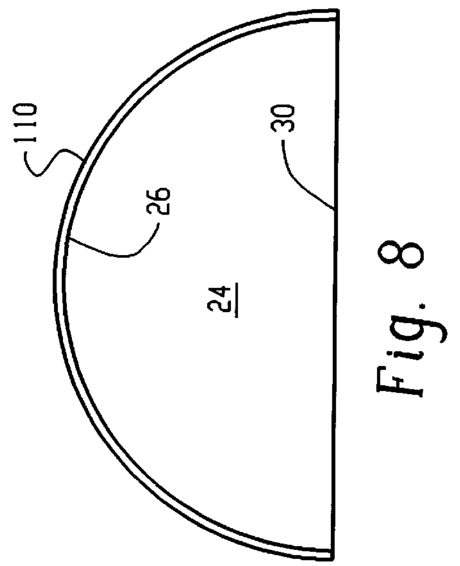
FIGS. 9A and 9B are top views of the optical sensor in accordance with the present invention wherein more than one optical fiber is employed for inputting light into the optical element and for receiving light from the optical element; and, FIG. 10 is a diagrammatic illustration of the optical sensor in accordance with the present invention wherein the light source and photodetector are mounted directly to the optical element.
Figure 9B:
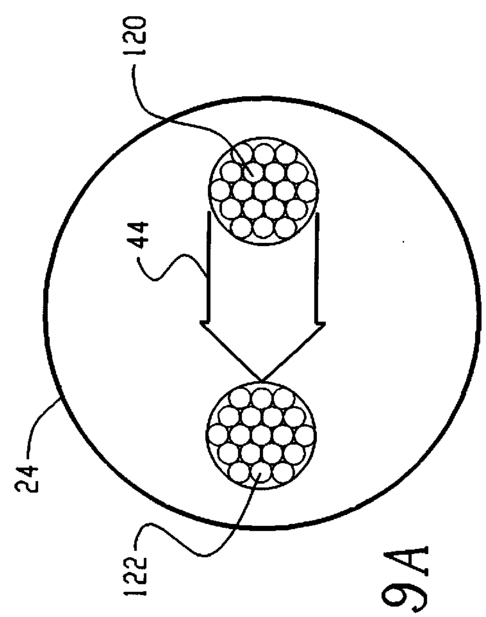

With reference to FIGS. 9A and 913, although only a single input and a single output optical fiber have been described heretofore, it is to be appreciated that more than two optical fibers may be utilized. Bundles of input and output optical fibers may be connected to a common optical element. That is to say, a bundle of input optical fibers 120 may be positioned opposite a bundle of output optical fibers 122 across from the center of the coupling surface 30 of the optical element 24 as shown in FIG. 9A. Alternatively, a plurality of input optical fibers 124*a–d* may be positioned across from a corresponding plurality of output optical fibers 124*a–d* on opposite sides of the center of the coupling surface of the optical element as shown in FIG. 9B. In this manner, each individual input optical fiber has corresponding output optical fiber positioned symmetrically about and equidistant from the center of the coupling surface.

Figure 10:
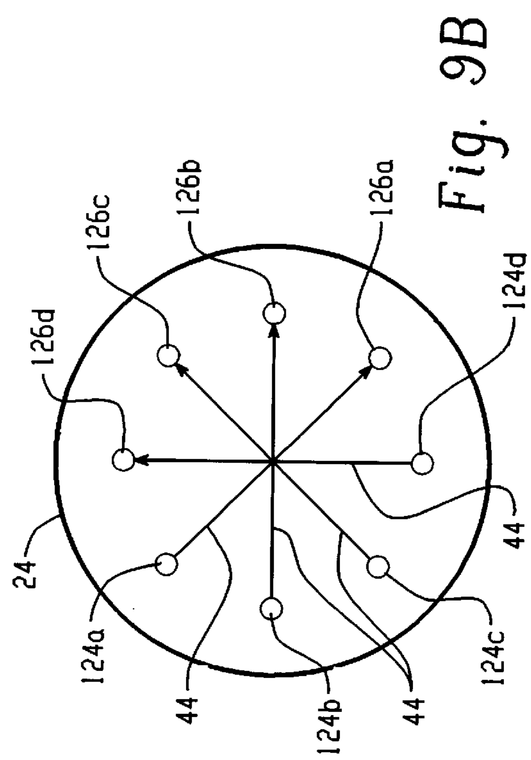

With reference to FIG. 10, in another preferred embodiment, the optical fibers 22 and 28 are disposed of and either the light source 20 or the photodetector 50 or both are mounted directly onto the coupling surface 30 of the optical element 24. This configuration is arranged so that light source 20 and photodetector 50 are directly coupled to the optical element 24 such that the light paths are analogous to those in which the optical fibers are employed. This embodiment is particularly advantageous where compact design is desirable.

While the optical sensor 10 herein has been referred to as having partial reflections at the measuring surface 26, in an alternative embodiment there is full transmission of the light at the measuring surface 26 when the monitored substance 12 has the appropriate index of refraction. That is to say, that in this alternate embodiment the optical sensor 10 acts as a null sensor. The sensor in this case is designed to monitor for a particular index of refraction (or a substance having that particular index of refraction). The optical element 24 is chosen from a material having the index of refraction matching the desired index of refraction being monitored. In this manner, when a substance having the same index of refraction as the optical element 24 is in contact with the measuring surface 26 there is full transmission of the light because there is no difference in the index of refraction. Consequently, there is minimal-to-no reflection. Therefore, when the photodetector is nulled or receiving minimal light from the optical element 24, the substance being monitored 12 is known to have substantially the same index of refraction as the optical element 24. Hence, by employing an appropriate look-up table the substance is identified.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An optical sensor for determining an index of refraction of a substance being monitored comprising:

a light source;

an optical element having a planar coupling surface and a convex measuring surface, wherein an input divergent beam of light entering the optical element through the coupling surface is partially reflected twice from the measuring surface such that it is focused at and exits through the coupling surface;

an input optical fiber having first and second ends, the first end optically coupled to the coupling surface of the optical element and the second end optically coupled to the light source, wherein the input optical fiber directs light emitted from the light source to the optical element such that it enters the optical element through the coupling surface to form the input divergent beam of light; and, an output optical fiber having first and second ends, the first end optically coupled to the coupling surface of the optical element and the second end optically coupled to a photodetector, such that the output optical fiber directs light focused at and exiting through the coupling surface of the optical element to the photodetector.

2. The optical sensor of claim 1, wherein an amount of light that is partially reflected at each reflection from the measuring surface is dependent on a difference between an index of refraction of the optical element and the index of refraction of the substance being monitored which is adjacent the measuring surface of the optical element.

3. The optical sensor of claim 1, wherein the convex measuring surface is a substantially spherical surface segment.

4. The optical sensor of claim 1, wherein the optical element is made of sapphire.

5. The optical sensor of claim 1, wherein the input and output optical fibers are arranged such that central axes of their first ends are parallel to one another and are both normal to a plane defined by the coupling surface of the optical element.

6. The optical sensor of claim 5, wherein the first ends of the input and output optical fibers are positioned symmetrically on opposite sides of and equidistant from a center of the coupling surface of the optical element.

7. The optical sensor of claim 1, wherein the light source is a light emitting diode.

8. The optical sensor of claim 1, wherein the measuring surface of the optical element is coated with a coating that interacts with a preselected target substance thereby changing its reflectivity.

9. The optical sensor of claim 1, further including:

circuitry connected to the photodetector to receive a signal therefrom which corresponds to an amount of light received by the photodetector, wherein the circuitry compares the signal while the measuring surface is in contact with the substance being monitored to a known value which would be received were the measuring surface in contact with a calibration substance having a known index of refraction.

10. The optical sensor of claim 9, wherein the circuitry addresses a corresponding index of refraction from a table which maps a ratio of the signal received to the known value on a scale versus index of refraction.

11. The optical sensor of claim 1, wherein the first ends of the input and output optical fibers are secured within a holder such that they are in abutting relationship with the planar coupling surface of the optical element.

12. The optical sensor of claim 11, wherein the holder comprises:

a plug having a pair of axial bores along its length, said optical element being secured to an end of the plug; and, capillary tubes secured within the axial bores, said capillary tubes holding the first ends of the input and output optical fibers therein.

13. The optical sensor of claim 12, wherein the capillary tubes are contained entirely within the axial bores.

14. The optical sensor of claim 11, wherein the holder is provided with threads around a periphery thereof such that the optical sensor is installable through a wall upon one side of which is located the substance being monitored.

15. An optical sensor for determining an index of refraction of a substance being monitored comprising:

a light source;

an optical element having a coupling surface and a measuring surface, wherein an input divergent beam of light entering the optical element through the coupling surface is partially reflected twice from the measuring surface such that it is focused at and exits through the coupling surface;

an input optical fiber having first and second ends, the first end optically coupled to the coupling surface of the optical element and the second end optically coupled to the light source, wherein the input optical fiber directs light emitted from the light source to the optical element such that it enters the optical element through the coupling surface to form the input divergent beam of light; and, an output optical fiber having first and second ends, the first end optically coupled to the coupling surface of the optical element and the second end optically coupled to a photodetector, such that the output optical fiber directs light focused at and exiting through the coupling surface of the optical element to the photodetector;

wherein the input and output optical fibers are arranged such that central axes of their first ends are parallel to one another and are both normal to a plane defined by the coupling surface of the optical element;

wherein the first ends of the input and output optical fibers are positioned symmetrically on opposite sides of and equidistant from a center of the coupling surface of the optical element; and, wherein the first ends of the input and output optical fibers are arranged such that extensions of their central axes intersect the measuring surface at 45° relative to a normal of the measuring surface at the intersection points.

16. A method of sensing the index of refraction of a monitored substance comprising:

(a) generating light;

(b) directing the light to a first planar surface of an optical element;

(c) transmitting the light into the optical element through the first planar surface of the optical element such that it forms a divergent beam;

(d) directing the light to a second convex surface of the optical element which is in contact with a calibration substance having a known index of refraction;

(e) transmitting a portion of the light into the calibration substance and reflecting a remaining portion of the light, said reflection also performing a focusing action on the remaining portion of the light;

(f) directing the remaining portion of the light from step (e) to another portion of the second convex surface of the optical element;

(g) repeating step (e);

(h) directing the remaining portion of the light from step (g) to the first planar surface of the optical element where the focusing action has substantially focused the remaining portion of the light;

(i) expelling the light from the optical element through the first planar surface;

(j) measuring an amount of expelled light;

(k) storing the measurement from step (j) in a memory;

(l) repeating steps (a)–(j) while the second convex surface of the optical element is in contact with the monitored substance;

(m) computing a ratio of the measured amount of expelled light from step (1) to the stored measurement from step (k); and.

(n) retrieving a corresponding index of refraction for the monitored substance from a table which maps on a scale the computed ratio versus index of refraction.

17. The method of claim 16, further including:

in step (d), directing the light to a first region which lies within one half of the second convex surface of the optical element; and, in step (f), directing the remaining portion of the light from step (e) to a second region which lies within an opposing half of the second convex surface of the optical element.

18. The method of claim 16, further comprising:

(o) determining from the retrieved index of refraction whether petroleum products are present in the monitored substance.

19. The method of claim 18, further comprising:

(p) displaying names of the petroleum products determined to be present in the monitored substance.

* * * * *